(12) United States Patent
Atlas et al.

(10) Patent No.: US 9,763,777 B2
(45) Date of Patent: Sep. 19, 2017

(54) DEVICE FOR EAR DRUM REPAIR

(75) Inventors: Marcus Atlas, West Leederville (AU); William Brett Robertson, Cottesloe (AU); Robert Jeffrey Marano, Willagee (AU); Sharon Leanne Redmond, Heathridge (AU); Peter Luke Santa Maria, Redwood City, CA (US); Brett Levin, Avalon (AU); Bing Mei Teh, Subiaco (AU)

(73) Assignee: EAR SCIENCE INSTITUTE AUSTRALIA, Subiaco, Western Australia (AU)

( * ) Notice: Subject to any disclaimer, the term of this patent is extended or adjusted under 35 U.S.C. 154(b) by 0 days.

(21) Appl. No.: 14/131,710

(22) PCT Filed: Jul. 11, 2012

(86) PCT No.: PCT/AU2012/000830
§ 371 (c)(1),
(2), (4) Date: May 20, 2014

(87) PCT Pub. No.: WO2013/006908
PCT Pub. Date: Jan. 17, 2013

(65) Prior Publication Data
US 2014/0303727 A1    Oct. 9, 2014

(30) Foreign Application Priority Data

Jul. 11, 2011  (AU) ................................ 2011902758
Oct. 27, 2011  (AU) ................................ 2011904474

(51) Int. Cl.
*A61F 2/18*    (2006.01)
*A61L 27/22*   (2006.01)
(Continued)

(52) U.S. Cl.
CPC .............. *A61F 2/18* (2013.01); *A61L 27/227* (2013.01); *A61L 27/24* (2013.01); *A61L 27/38* (2013.01);
(Continued)

(58) Field of Classification Search
CPC ........................... A61F 2/18; A61F 2002/183
See application file for complete search history.

(56) References Cited

U.S. PATENT DOCUMENTS 4,169,292 A * 10/1979 Grote .............................. 623/10
5,141,747 A    8/1992 Scholz
(Continued)

OTHER PUBLICATIONS

International Search Report for PCT/AU2012/000830 dated Aug. 20, 2012.
Daphalapurkar Nitin P et al, Characterization of the Linearly Viscoelastic Behavior of Human Tympanic Membrane by Nanoindentation, Journal of the mechanical behavior of biomedical materials, Netherlands, (Jan. 2009), vol. 2, pp. 82-92.
(Continued)

*Primary Examiner* — Katrina Stransky
*Assistant Examiner* — Wade P Schutte
(74) *Attorney, Agent, or Firm* — Stephen J. Weyer, Esq.; Stites & Harbison, PLLC.

(57) ABSTRACT

A device for use in the repair of an ear drum in a subject in need of such treatment, said device: having a tensile strength Youngs Modulus between approximately 12.5 and 40 MPa; comprising one or more membrane layers, wherein at least one membrane layer comprises a plurality of pores; and wherein the device can support proliferation, migration and/or adhesion of cells selected from the group comprising at least any one or more of: keratinocytes, fibroblasts, vascular cells, mucosal epithelial cells, and stem cells.

20 Claims, 4 Drawing Sheets

(51) Int. Cl.
*A61L 27/24* (2006.01)
*A61L 27/38* (2006.01)
*A61L 27/50* (2006.01)
*A61L 27/54* (2006.01)
*A61L 27/56* (2006.01)
*A61B 17/00* (2006.01)

(52) U.S. Cl.
CPC ............. *A61L 27/50* (2013.01); *A61L 27/54* (2013.01); *A61L 27/56* (2013.01); *A61B 2017/00787* (2013.01); *A61F 2002/183* (2013.01); *A61L 2300/236* (2013.01); *A61L 2300/252* (2013.01); *A61L 2300/414* (2013.01); *A61L 2300/426* (2013.01); *A61L 2430/14* (2013.01)

(56) References Cited

U.S. PATENT DOCUMENTS

| | | | |
|---|---|---|---|
| 8,889,179 | B2 | 11/2014 | Coffey et al. |
| 8,992,594 | B2 * | 3/2015 | Soletti .................. A61B 17/11 623/1.13 |
| 2003/0054035 | A1 | 3/2003 | Chu et al. |
| 2003/0133967 | A1 | 7/2003 | Ruszczak et al. |
| 2007/0038298 | A1 | 2/2007 | Sulner et al. |
| 2010/0286774 | A1 | 11/2010 | Kweon et al. |
| 2011/0166325 | A1 | 7/2011 | Saeidi et al. |

OTHER PUBLICATIONS

Supplementary European Search Report dated Feb. 6, 2015 in corresponding European Patent Application No. 12 81 1708.

* cited by examiner

Figure 1

Normal Eardrum

DEVICE FOR EAR DRUM REPAIR

FIELD OF THE INVENTION

The present invention relates to a device for use in the repair of an ear drum, and particularly in the repair of tympanic membrane perforations and reconstruction of the pars flaccida. It also relates to methods for repairing damage to an ear drum, and particularly in the repair of tympanic membrane perforations.

BACKGROUND ART

The following discussion of the background art is intended to facilitate an understanding of the present invention only. The discussion is not an acknowledgement or admission that any of the material referred to is or was part of the common general knowledge as at the priority date of the application.

Tympanic membrane perforation is one of the most common problems in otolaryngology. If left untreated, it is associated with significant morbidity such as hearing loss, recurrent otorrhea, middle ear infection and acquired cholesteatoma. Although most acute tympanic membrane perforations heal spontaneously, large or chronic tympanic membrane perforations, especially from chronic suppurative otitis media, often fail to heal and may require grafting.

In cases of chronic tympanic membrane perforation, a surgical procedure known as myringoplasty (or type I tympanoplasty) is required for closure of the perforation. Myringoplasty involves the use of a graft to "patch the perforation" and restore the integrity of the tympanic membrane; the purpose of which is to restore the continuity of the tympanic membrane to improve hearing and decrease the incidence of further middle ear infection.

Typically, an autograft (tissue obtained from the subject) is used with the most common type being temporalis fascia, which is considered the "gold standard" for tympanic membrane closure. Other types of commonly used autografts include cartilage, perichondrium and fat, and despite many studies comparing the efficacy of the various materials, there does not seem to be a clear consensus as to which is superior. Most purport success rates up to 90% regardless of the graft material or technique used. Despite this high success rate, reasons for graft failure may include instances of reperforation, cholesteatoma, lateralization, blunting, epithelial pearl and inclusion cysts.

Aside from this, there are other drawbacks associated with myringoplasty; it can be expensive, due to the requirement of anesthesia, surgery and an overnight hospital admission; has inherent morbidity and possible issues with defective donor sites. In addition, it has been recently argued that what is considered a success should be reviewed to include conditions of the middle ear, such as effusion, atelactasis and discharge, which could adversely affect the outcome. Transparency of the tympanic membrane has also been indicated as a factor that affects hearing with opaque membranes resulting in significantly higher hearing thresholds. Opacity was the result of thickening of the tympanic membrane; and increased thickness results in greater stiffness and diminished mobility. Similarly, autologous graft material tends to be opaque, thicker and more rigid than an undamaged tympanic membrane, adversely affecting acoustic transmission in addition to preventing the clinician from examining the middle ear for infection or defects during follow up.

The ongoing function of the repair may be influenced by the continued processes of retraction, cholesteatoma or reperforation and infection. Permanent conductive hearing loss can be caused by these continuing processes leading to erosion of the ossicles. The most common surgical approach then is to perform a tympanoplasty with a thicker layer of cartilage to resist further retraction and progression to retraction pocket formation, perforation and cholesteatoma. The cartilage can be used as an underlay, inlay or overlay graft.

However, as a result, these available methods using existing graft materials insufficiently replicate the microstructure and properties of native ear drums, hence premorbid hearing is not restored when they are used to repair perforated ear drums.

Moreover, the ear canal also plays a major role in modulating sound that is incident upon the tympanic membrane. The sharp anterior tympanomeatal angle, where the oblique ear canal meets the tympanic membrane, can significantly alter the sound pressure levels and impedances at various sites in front of the drum, especially at high frequencies. For this reason, the repair or reconstruction of the pars flaccida of the ear drum from degradation or other damage to the tissue and/or bone is often carried out in collaboration with tympanic membrane perforation repair, with the aim of restoring acoustic transmission and therefore premorbid hearing.

To date, a range of xenografts and synthetic materials, including Gelfoam®, and paper patch have been investigated as suitable scaffolds to support the regeneration of tympanic membranes. However, there is little evidence to support any of these as optimal materials for various types of perforations. Moreover, several commercially available xenografts such as porcine small intestine submucsa may evoke an inflammatory response due to the remnant xenocellular components using serotonin. In addition, synthetic materials are generally non-biodegradable, and their biomechanical and material properties are different compared to the normal tympanic membrane, which may affect the long-term hearing function. Hence there is a need for new materials for repairing ear drums and tympanic membrane perforations.

SUMMARY OF THE INVENTION

In a first aspect, the present invention provides a device for use in the repair of an ear drum in a subject in need of such treatment, said device:
having a tensile strength Youngs Modulus between approximately 12.5 and 40 MPa; and comprising one or more membrane layers, wherein at least one membrane layer comprises a plurality of pores;
wherein the device can support proliferation, migration and/or adhesion of at least cells selected from the group comprising any one or more of: keratinocytes, fibroblasts, vascular cells, mucosal epithelial cells, and stem cells.

The device preferably has a tensile strength Youngs Modulus between approximately 15 and approximately 37 MPa, and more preferably, a tensile strength Youngs Modulus between approximately 25 and approximately 35 MPa. The device of the invention may be made from one or more materials that are non-autologous to the subject in need of such treatment. These one or more materials may be selected from one or more of the group comprising: silk fibroin; hyaluronic acid based hydrogels and films; calcium alginate; alginic acid; pluronic 127; poly(glycerol sebacate); collagen (type I/III); water soluble and insoluble chitosan; gelatin; polyethylene glycol; or decellularised tissue from mammalian membranes, including tympanic membrane, pericardium, periosteum, dermis, and muscle fascia. In a preferred form of the invention, the device is made from silk fibroin. In another preferred form of the invention, the device is made from collagen type I/III.

In one form of the invention, the device comprises three membrane layers. Preferably, one or more of the membrane layers of the device are fibrous layers.

The diameter of pores of the device are preferably between approximately 0.001 µM and approximately 1 µM. More preferably, the pores of the device are distributed substantially evenly across one or more layers of the device.

In a preferred form of the device, the one or more membrane layers form a substantially disc-like shape having two ovoid or substantially circular faces on opposing sides of the device. Preferably, one or both faces have a diameter of between approximately 3 mm and approximately 25 mm, and more preferably between approximately 10 mm and approximately 20 mm. Preferably, one or both ovoid faces of the device have diameters of approximately 9 mm and approximately 8 mm. Even more preferably, one or both ovoid faces of the device have diameters of approximately 6 mm and approximately 5 mm. Most preferably, one or both faces of the device are substantially circular and have a diameter of approximately 3 mm.

The one or more membrane layers of the device have a thickness which can be measured as the distance between the exposed faces of the one or more membranes on the exterior of the device. Preferably, the one or more membrane layers have a combined thickness of between approximately 10 and approximately 600 µM. More preferably, the one or more membrane layers have a combined thickness of between approximately 10 and approximately 100 µM. Most preferably, the one or more membrane layers have a combined thickness of between approximately 80 and approximately 100 µM.

In a preferred embodiment of the invention, the device comprises bioactive molecules, preferably wherein the bioactive molecules assist or promote the growth of cells of the ear drum. The bioactive molecules may be bound to the surface of the device or located in pores of the device.

The bioactive molecules may comprise any one or more bioactive molecules selected from the group comprising: vitamins, proteins, peptides, enzymes, carbohydrates, cofactors, nucleotides (DNA or RNA or derivatives thereof), small organic molecules (for example, drugs), antibiotics, antiviral agents, antimicrobial agents, anti-inflammatory agents, antiproliferative agents, cytokines, protein inhibitors, antihistamines. Preferably the bioactive molecules comprise any one or more bioactive molecules selected from the group comprising: epidermal growth factors including Epidermal Growth Factor (EGF), transforming growth factor-alpha (TGF-α), Heparin Binding Epidermal Growth Factor (HB-EGF), amphiregulin, epigen, epiregulin, betacellulin; fibroblast growth factors including acidic fibroblast growth factor (FGF-1/aFGF), basic fibroblast growth factor (FGF-2/bFGF); keratinocyte growth factors including Keratinocyte Growth Factor 1 (KGF-1/FGF-7), Keratinocyte Growth Factor 2 (KGF-2/FGF-10); insulin-like growth factors including Insulin-like Growth Factor 1 (IGF-1), Insulin-like Growth Factor 2 (IGF-2); platelet derived growth factors including. Vascular Endothelial Growth Factor 165 ($VEGF_{165}$), Platelet Derived Growth Factor-BB (PDGF-BB), cytokines including IL-6, IL-19, IL-24; extracellular matrix proteins including hyaluronic acid, fibronectin, vitronectin, laminin; and vitamins including trans-retinoic acid (vitamin A), L-ascorbic acid (vitamin C), (+)-α-tocopherol (vitamin E). More preferably, the bioactive molecules comprise any one or more bioactive molecules selected from the group comprising: hyaluronic acid; vitronectin; amphiregulin; interleukin 19 (IL-19); interleukin 24 (IL-24); transforming growth factor-alpha (TGF-α); VEGF; and fibronectin.

The concentration of bioactive molecules is preferably between 5 ng/ml and 150 µg/ml. Where present in the device, the concentration of hyaluronic acid is preferably between approximately 1 µg/ml and approximately 10 µg/ml, and more preferably at approximately 5 µg/ml. Where present in the device, the concentration of vitronectin is preferably between approximately 0.1 µg/ml and approximately 1.0 µg/ml, and more preferably at approximately 0.5 µg/ml. Where present in the device, the concentration of amphiregulin is preferably between approximately 20 ng/ml and approximately 100 ng/ml, and more preferably at approximately 60 ng/ml. Where present in the device, the concentration of IL-19 or IL-24 is between approximately 20 ng/ml and approximately 100 ng/ml, and more preferably at approximately 60 ng/ml. Where present in the device, the concentration of TGF-α is between approximately 20 ng/ml and approximately 140 ng/ml, and more preferably at approximately 80 ng/ml. Where present in the device, the concentration of VEGF is between approximately 60 ng/ml and approximately 200 ng/ml, and more preferably at approximately 100 ng/ml.

The bioactive molecules may be added during formation of the device and/or may be added separately to the device after the device is formed and/or during implantation or grafting of the device.

The membrane layers of the device may be formed during production of the device by at least any one or more of: spinning including electrospinning; weaving including microweaving; or casting. The membrane layers may be formed at the same time during production of the device or they may be formed separately before being attached during production of the device. Alternatively, membrane layers may be created by folding the device.

The device of the invention may be at least partially translucent, or partially or fully transparent, which can assist in post treatment examination of the ear drum and middle ear of a subject treated with the device.

In a preferred form, the device of the invention is biodegradable. More preferably, the device has a biological life of between 1 and 12 months.

The device of the invention may be trimmed post-production to match the size and shape of a region of the ear drum requiring repair, and this trimming may be carried out using an appropriate cutting device such as surgical scissors. The device may also be manipulated post production by scoring or cutting grooves in one or more surfaces of the device to improve the flexibility or bendability of the device, or to allow it to fold and substantially maintain its folded conformation.

In another aspect, the invention provides for the use of a device as herein described for supporting proliferation, migration and/or adhesion of at least the cells of an ear drum when grafted or applied to the ear drum of a subject, or more preferably, the tympanic membrane such as a perforated tympanic membrane of a subject, and/or the pars flaccida and/or the scutum bone proximal to the pars flaccida of a subject. The invention also provides for the use of a device as herein described in mastoid obliteration techniques for reconstruction of an ear canal of a subject after tympanomastoidectomy, including to cover a hydroxyapatite free graft.

In a further aspect, the invention provides a method for repairing the ear drum, and more preferably a tympanic membrane perforation such as a chronic tympanic membrane perforation, and/or a defective pars flaccida and/or the scutum bone proximal to the pars flaccida, in a subject in need of such treatment, said method comprising using the device as herein described.

The invention also provides a kit for use in the repair of an ear canal, a tympanic membrane perforation, and/or the pars flaccida of a subject, said kit comprising a device as herein described. The kit may also comprise one or more solutions of any of the bioactive molecules as herein described. The one or more solutions of bioactive molecules may be for application to the device prior to implantation of the device into a subject, or for application to the device following implantation or grafting of the device to the ear drum of the subject which may occur once, or on multiple occasions thereafter.

Thus, the device of the present invention provides a customised graft implant for use in the repair and regeneration of a perforated tympanic membrane and/or the reconstruction and regeneration of the ear canal including the pars flaccida and scutum bone in a subject in need of such treatment. Customisation of the device can assist in facilitating regeneration of the ear drum including the tympanic membrane and/or ear canal to substantially resemble the native form thereby enabling better opportunity for improved healing and hearing outcomes for a subject. Inclusion of the fibrous middle layer in the device is particularly beneficial in making the tympanic membrane acoustically more efficient, whilst reducing the potential for atrophy, reperforation and cholesteatoma formation in the subject.

DETAILED EMBODIMENTS OF THE INVENTION

General

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness. None of the cited material or the information contained in that material should, however be understood to be common general knowledge.

Manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (e.g. size, concentration etc.). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

Reference to cited material or information contained in the text should not be understood as a concession that the material or information was part of the common general knowledge or was known in Australia or any other country.

Features of the invention will now be discussed with reference to the following non-limiting description and examples.

The present invention provides a device for use in the repair of an ear drum in a subject in need of such treatment, said device:
  having a tensile strength Youngs Modulus between approximately 12.5 and 40 MPa; and comprising one or more membrane layers, wherein at least one membrane layer comprises a plurality of pores;
wherein the device can support proliferation, migration and/or adhesion of at least cells selected from the group comprising any one or more of: keratinocytes, fibroblasts, vascular cells, mucosal epithelial cells, and stem cells.

The repair of the ear drum preferably comprises the repair of a tympanic membrane perforation, and particularly a chronic perforation. The repair of the ear drum may in addition or alternatively comprise repair of the ear canal, and in particular the pars flaccida and/or the scutum bone proximal to the pars flaccida of the subject.

It is preferable that the device can support proliferation, migration and/or adhesion of at least the above described cells when grafted to the perforated tympanic membrane or ear canal of a subject in need of such treatment. This is in order to facilitate the repair and regeneration of the tympanic membrane from damage such as from a chronic perforation. Thus, the device of the invention provides a framework to enable the accelerated closure of a chronic tympanic membrane perforation or a defective portion of ear canal soft tissue and bone via natural wound healing processes.

Figure 1:
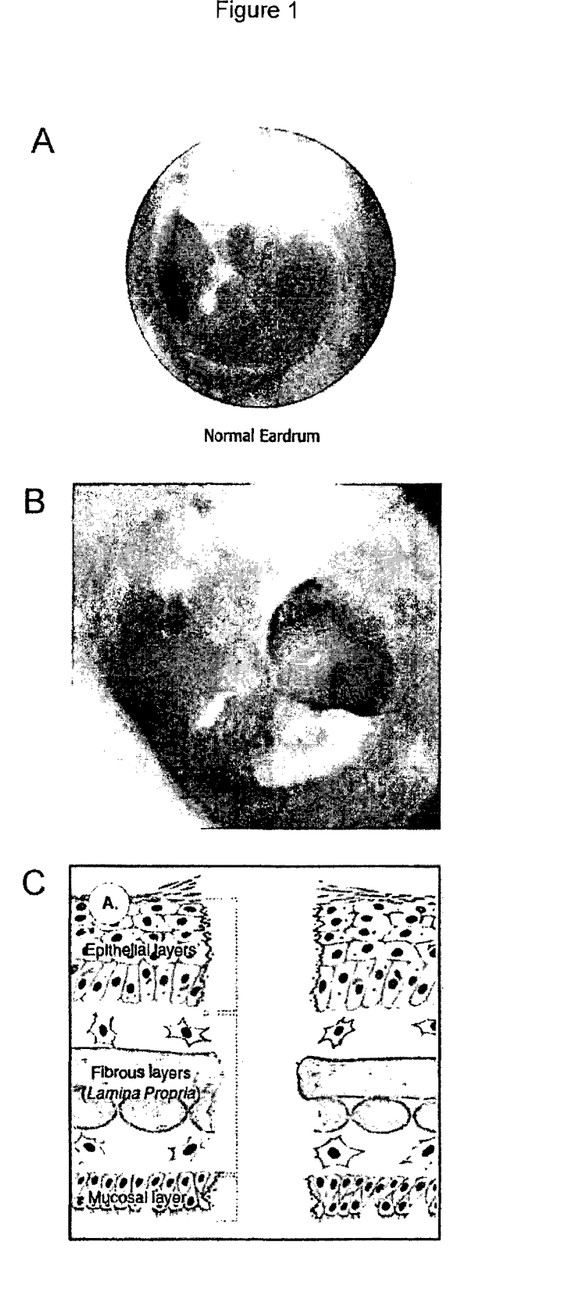
FIG. 1: A perspective view of an illustration of a preferred form of the device.

For the purposes of describing the device of the invention and how it may be used, the term "perforated", "perforation" or any other variation of "perforate" thereof will be understood to include any damage to the tympanic membrane of a subject that can be repaired using the device of the invention. In some non-exhaustive examples, such damage may include a hole or tear in the tympanic membrane or a deformity or loss of any part of the membrane or a layer of a membrane as a result of physical forces or disease (see for example FIG. 1). The tympanic membrane forms part of the eardrum which comprises the pars tensa, and pars flaccida in the posterior ear canal. The pars flaccida is also referred to as the attic and includes within this region, soft tissue of the ear canal and surrounding scutum bone. For the purposes of describing the device of the invention and how it may be used, the term "defective" or any other such variation of the term thereof will be understood to include any damage or disease to the soft tissue or bone of the pars flaccida or surrounding area of a subject, that can be repaired or reconstructed using the device of the invention. This may include, damage or disease from cholesteatoma, or necessary repair of an ear canal of a subject following mastoidectomy, amongst others.

Shape of the Device

The device of the invention may be formed into any size, shape or conformation that will facilitate its use in the repair of a perforated tympanic membrane or a defective portion of ear canal soft tissue and bone. For example, the device can be formed into any size, shape or conformation that will facilitate the occlusion of a tympanic membrane perforation, particularly in the context of a tympanoplasty or myringoplasty.

In another example, the device can be formed into any shape or conformation that will facilitate the reconstruction of the ear canal, such as the pars flaccida and attic region. This may include folding of the device or scoring of one or more sides of the device such that the modified conformation of the device is maintained. Thus, the size, shape and conformation of the device will be sufficient to cover or fit within the defective portion of ear canal.

Figure 2:
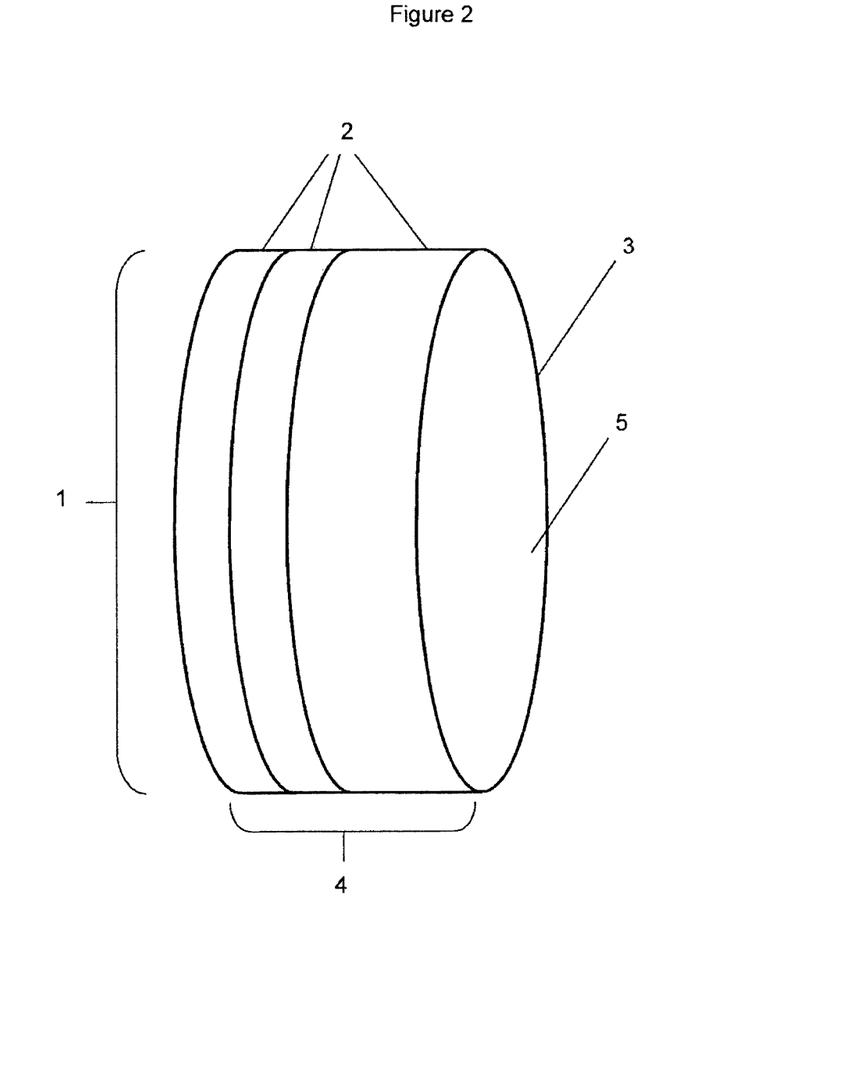
FIG. 2: A front view of an illustration of three forms of the device prepared by methods of weaving, spinning and casting resulting in pores of different sizes and shapes. Exploded views of a section of the three variations of the device are shown to highlight the shapes of pores produced by these methods of preparation. Preferred diameters of the device are also shown.

A preferred form of the device of the invention is illustrated in FIG. 2 showing a substantially disc-like shape or conformation 1 comprising three membranes 2 having an ovoid or substantially circular front face 3 layered adjacent to each other resulting in the device having a thickness 4.

The front face of a device of the invention may alternatively be of a shape other than ovoid or circular which could be selected according to the dimensions of a tympanic membrane perforation or defective portion of ear canal.

Figure 3:
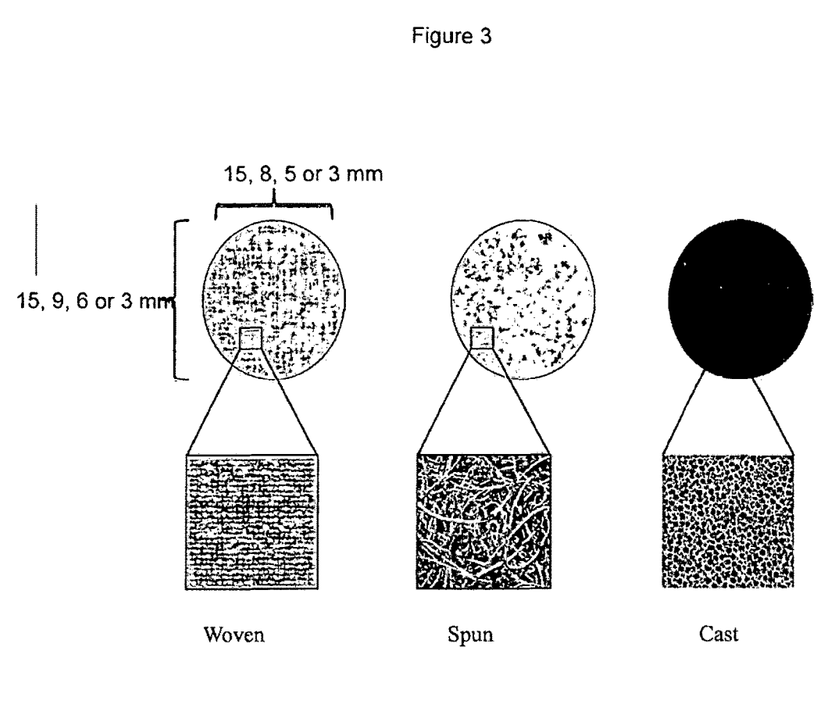
FIG. 3: An otoscope image of (A) a normal eardrum, and (B) a perforated human eardrum requiring repair. (C) is an illustration depicting the side view of the damaged edge of a perforated tympanic membrane and the types and position of cells that would be present.

The front face of the device of the invention may comprise a variety of sizes. In a preferred form of the device, the front face is an ovoid shape or substantially circular shape having a diameter of approximately 10 mm to 20 mm, and more preferably a diameter of approximately 15 mm. In another form of the device, the front face is an ovoid shape having a diameter of approximately 9 mm×approximately 8 mm. In a second preferred form of the device, the front face is an ovoid shape of approximately 6 mm×approximately 5 mm. In a third preferred form of the device, the front face is a substantially circular shape with a diameter of approximately 3 mm (FIG. 3). The device may be trimmed from around the outer edge of the front fate 5 thereby customising said device for repair of a tympanic membrane perforation or defective portion of ear canal that is smaller than an available device.

One or both faces of the device may be scored or grooves cut using a variety of different tools including cutting tools such as scissors or a knife or blade.

Thickness

The device may be of variable thickness 4. The thickness of a device of the invention may vary depending on factors such as the number of membrane layers, or the size of the tympanic membrane perforation or defective portion of ear canal in a subject treated using the device. In a preferred embodiment, the device has a thickness of between approximately 10 and approximately 600 μM. More preferably, the device has a thickness of between approximately 10 and approximately 100 μM. The thickness of the device is most preferably between approximately 80 and approximately 100 μM.

In a preferred form of the device, the thickness of the device is between approximately 10 and approximately 100 μM, and more preferably between approximately 80 and approximately 100 μM. The thickness of the device may depend on the number of membrane layers 2 in the device.

Tensile Strength

A membrane of the device of the invention may possess a range of stiffness/tensile strength Youngs Modulus of 12.5 MPa to 40 MPa and this value may be selected so as to substantially match size of perforation and acoustic properties. A tensile strength Youngs Modulus of approximately 12.5 MPa is similar to the tensile strength Youngs Modulus of a native tympanic membrane. In a preferred embodiment, the device of the invention has a stiffness/tensile strength Youngs Modulus of 20 MPa to 37 MPa. More preferably, the device of the invention has a stiffness/tensile strength Youngs Modulus of 25 MPa to 35 MPa. This is particularly useful for treating perforations in the par tensa which is the most common area for a perforation. Sound transmission to the middle ear ossicles is dependent on the "stiffness" of a graft comprising the device and is an important issue in large perforations for an instant improvement in hearing outcomes. The specific tensile strength of the one or more membranes facilitates optimal acoustic transmission resulting in improved hearing outcomes for a subject treated with the device immediately following placement.

Composition

The at least one membrane layer may be produced from a range of different materials. For the purposes of describing the invention, the terms "membrane layer" and "layer" may be used interchangeably. These materials may be of a source non-autologous to the subject treated with the device. More preferably, the materials are of a non-mammalian source and may include a range of biocompatible materials that will support proliferation, migration and/or adhesion of tympanic membrane keratinocytes following in vivo implantation as well as in vitro culture. Preferably, biomaterials are selected that provide that the device is relatively soft.

In a preferred form of the device, the membranes comprise the biomaterial silk fibroin. Silk fibroin, a protein polymer obtained from silkworm silk, possesses properties including biocompatibility, biodegradability, high tensile strength and elasticity, and on which human tympanic membrane keratinocytes can grow. The silk fibroin may be used to manufacture membranes of the device through weaving, casting and electrospinning techniques to create different pore shapes and sizes in the device as discussed above. Silk fibroin is easily manipulated due to its physical and chemical properties.

Other materials which may be used to produce the device include any of the materials selected from the group comprising: hyaluronic acid based hydrogels (Carbylan) and films (Seprafilm); calcium alginate; poly(glycerol sebacate); water soluble and insoluble chitosan; and collagen. In this respect, collagen, a major extracellular matrix component, has physical characteristics including high tensile strength, flexibility, non-reactivity, non-toxicity and non-carcinogenicity. As the main constituent of the lamina propria of the tympanic membrane, collagen helps to maintain the resilience and integrity of tympanic membrane and hence plays a key role in hearing.

The device of the invention may further comprise one or more additive selected from the group comprising, amongst others, collagen, gelatin, chitosan, alginic acid, hyaluronic acid, pluronic 127 and polyethylene glycol in order that the device is manageable in a dry state prior to use.

The device of the invention may further comprise one or more additive selected from the group comprising, amongst others, decellularised tissue from mammalian membranes, including tympanic membrane, pericardium, periosteum, dermis, muscle fascia.

Structure and Mechanical Properties

There are various methods for preparing the device of the invention. Such methods may include preparing the device from woven, non-woven and/or electrospun materials. Woven methods may include the use of a microweaving device similar to a standard textile loom albeit on a micro scale. The result is a substantially orderly woven material. Non-woven methods may include casting, amongst others. Casting involves placing a volume of solubilised fibroin solution into a casting vessel and allowing the liquid to evaporate, leaving behind a solid cast of the fibroin protein. Electrospinning uses an electrical charge to draw very fine (micro or nano scale) fibroin fibres from a liquid solution of the protein. It is particularly suited to the production of fibers using large and complex molecules. These methods for preparing the device produce pores within and on the surface of the device. Shapes and sizes of the pores will vary depending on the method used to prepare the device (FIG. 2B). Preferred pore size on the device of the present invention will range between a diameter of approximately 0.001 µm and approximately 1 µm although smaller or larger pore sizes may be used in the device of the invention. Selecting an appropriate pore size is important to facilitate cellular adhesion for efficient growth and proliferation across the device and at the same time to prevent infiltration of keratinocytes through the device and into the middle ear when in use, which may promote cholesteatoma. More preferably, the pores in the middle layer of a device of the invention have a diameter of between approximately 20 µm and approximately 200 µm to facilitate cell infiltration and tissue formation of the middle layer.

The pores of the device are present to provide void volume for vascularisation, new tissue formation and remodeling so as to facilitate host tissue integration upon implantation into a subject in need of such treatment. In this respect, the device provides a structure that is porous for efficient nutrient and metabolite transport whilst also maintaining mechanical stability. Preferably there is a substantially consistent distribution of pores across the surface of at least one membrane layer of the device.

Similarly to an undamaged tympanic membrane, the device of the invention may be transparent or translucent. This also enables examination of the middle ear of a subject for infection or defects during follow up after repair of the tympanic membrane using the device.

It is preferable that the device of the invention has vibroacoustic characteristics similar to that of a native tympanic membrane and when used in repair of a tympanic membrane of a subject in need of such treatment, can transmit sound waves between 20 Hz and 20 KHz to the middle ear ossicles. Such vibroacoustic characteristics are related to the tensile strength, elasticity and the thickness of the device, and are preferably optimized for the conduction of sound. Having such vibroacoustic characteristics would enable the device to vibrate in a similar way as the native tympanic membrane, thereby restoring the properties of the overall tympanic membrane structure.

Layers

In a preferred form of the device, between one and three membranes are layered adjacent to each other. However, a device of the invention may include more than three layers.

For a three membrane layered device, it is preferable that the second (i.e. middle) layer is fibrous. In a preferred form of the device, the device comprises silk fibroin and the term 'fibrous' relates to the arrangement of the fibroin strands within the layer. It would appear as a random arrangement of microfine fibroin strands achieved using the spinning process as opposed to an ordered arrangement achieved through weaving or a smooth appearance resulting from the casting method (see FIG. 3). For a two membrane device, it is preferable that one layer is fibrous and this layer will face the middle ear upon graft of the device in a subject. The number of membranes in a device may be selected according to the size of a tympanic membrane perforation or defective portion of an ear canal.

For example, while a single layered membrane may be sufficient in the repair of a small perforation of a tympanic membrane in a subject in need of such treatment, a three-layered approach may be preferred for large perforations to enable the reconstruction of the three layers of the native tympanic membrane. A single layer for large perforations can result in a single layered and flaccid neo-tympanum possessing poor acoustic properties.

In another example, in the repair of a defective portion of the soft tissue and/or bone of an ear canal such as the attic, the three-layered approach may be preferred to reconstruct the canal. Alternatively, more than one device of the invention, or a folded device of the invention may be preferable to match the size of the defective portion of the ear canal.

Bioactive Molecules

The device of the invention may comprise, for example, be impregnated with or coated with, one or more bioactive molecules which includes medicinal compounds. These bioactive molecules may comprise, amongst others, vitamins, proteins, peptides, enzymes, carbohydrates, co-factors, nucleotides (DNA or RNA or derivatives thereof), small organic molecules (for example, drugs), antibiotics, antiviral agents, antimicrobial agents, anti-inflammatory agents, anti-proliferative agents, cytokines, protein inhibitors, antihistamines or a combination of any of these. Preferred bioactive molecules of the device of the invention may comprise one or more from the group comprising: epidermal growth factors including Epidermal Growth Factor (EGF), TGF-α, Heparin Binding Epidermal Growth Factor (HB-EGF), amphiregulin, epigen, epiregulin, betacellulin; fibroblast growth factors including acidic fibroblast growth factor (FGF-1/aFGF), basic fibroblast growth factor (FGF-2/ bFGF); keratinocyte growth factors including Keratinocyte Growth Factor 1 (KGF-1/FGF-7), Keratinocyte Growth Factor 2 (KGF-2/FGF-10); insulin-like growth factors including Insulin-like Growth Factor 1 (IGF-1), Insulin-like Growth Factor 2 (IGF-2); platelet derived growth factors including Vascular Endothelial Growth Factor (VEGF$_{165}$), Platelet Derived Growth Factor-BB (PDGF-BB), cytokines including IL-6, IL-19, IL-24; extracellular matrix proteins including hyaluronic acid, fibronectin, vitronectin, laminin; and vitamins including trans-retinoic acid (vitamin A), L-ascorbic acid (vitamin C), (+)-α-tocopherol (vitamin E). The above bioactive molecules are preferably used in the device at a concentration in the range between approximately 5 ng/mL and approximately 150 µg/mL. More preferably, the device is coated or impregnated with at least one of hyaluronic acid, vitronectin, fibronectin, transforming growth factor-alpha (TGF-α), interleukin 19 (IL-19), interleukin 24 (IL-24). The concentration of hyaluronic acid which can be used in the device of the invention is preferably between approximately 1 µg/mL and approximately 10 µg/mL, and more preferably at a concentration of approximately 5 µg/mL. The concentration of vitronectin which can be used in the device of the invention is preferably between approximately 0.1 µg/mL and approximately 1.0 µg/mL, and more preferably at a concentration of approximately 0.5 µg/mL. The concentration of amphiregulin which can be used in the device of the invention is preferably between approximately 20 ng/mL and approximately 100 ng/mL, and more preferably at a concentration of approximately 60 ng/mL. The concentration of IL-19 which can be used in the device of the invention is preferably between approximately 20 ng/mL and approximately 100 ng/mL, and more preferably at a concentration of approximately 60 ng/mL. The concentration of IL-24 which can be used in the device of the invention is preferably between approximately 20 ng/mL and approximately 100 ng/mL, and more preferably at a concentration of approximately 60 ng/mL. The concentration of TGF-α which can be used in the device of the invention is preferably between approximately 20 ng/mL and approximately 140 ng/mL, and more preferably at a concentration of approximately 80 ng/mL. The concentration of VEGF which can be used in the device of the invention is preferably between approximately 60 ng/mL and approximately 200 ng/mL, and more preferably at a concentration of approximately 100 ng/mL. Bioactive molecules that perform a similar function to said preferred bioactive molecules may also be used in addition or in the place of said preferred bioactive molecules. Concentrations of these molecules may be varied to optimise proliferation, migration or remodelling, depending on the combination present and will preferably be in amounts effective for treatment of tympanic membrane perforations or defective portions of the ear canal. In a preferred embodiment of the invention, concentrations of bioactive molecules including those described above may be added to solubilised silk fibroin, prior to casting, weaving or spinning the device. In another embodiment, the bioactive molecules may be applied as a solution to the surface of a membrane prior to implantation. Such impregnation or coating may be accomplished by any means known in the art, and a portion or the whole of the device may be so impregnated or coated.

The device may comprise any of the compounds listed herein, without limitation, individually or in any combination. Any of the bioactive molecules listed herein may be formulated by known methods for immediate release or extended release. Additionally, the device may comprise two or more bioactive molecules in different manners, for example, amongst others, the device may be impregnated with one biologically active compound and coated with another. In another embodiment, the device comprises one bioactive molecule formulated for extended release, and a second biologically active compound formulated for immediate release.

Wound healing including the repair of tympanic membranes requires sufficient nutrition. Wound healing nutrients include a source of zinc, iron, vitamin C, arginine, and other bioactive molecules. Therefore, the device may be impregnated or coated with a physiologically-available form of one or more of these nutrients required for wound healing. It is preferred that these nutrients are formulated for extended release.

In a preferred embodiment, proteins, polypeptides or peptides (including antibiotics) that are utilised as immunomodulatory agents are preferably derived from the same species as the subject in need of repair to the tympanic membrane or defective portions of the ear canal. For example, where the subject is a human, the proteins, polypeptides or peptides that are used as immunomodulatory agents are preferably human or humanised to reduce the likelihood of an immune response to the proteins, polypeptides or peptides.

Figure 4:
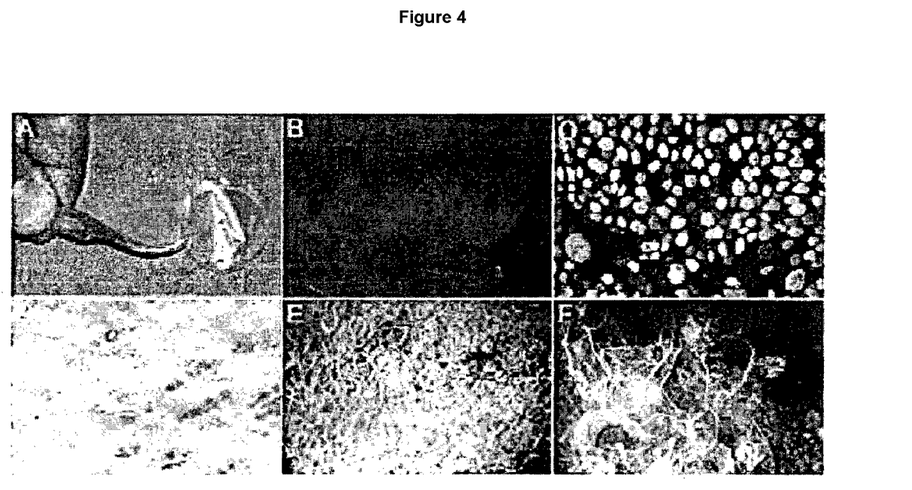
FIG. 4: Human tympanic keratinocytes grow on silk fibroin membranes. (A) a photograph of a transparent silk fibroin membrane device. The silk fibroin has proven successful as a substrate for adhesion and growth of human TM keratinocytes (B, adherent cells are stained blue). Staining for cell proliferation marker (C, Mib-1$^+$ nuclei green) shows that the silk membrane supports expansion of the cell population. Scanning electron microscopy shows that hTM keratinocytes grow to confluency as a complete sheet. Expression of adhesion junction proteins E-cadherin (E, green) or occludin (F, green) and ZO-1 (F, red) was localised to the cytoplasmic membranes of all cells.

Bioactive molecules are considered to enhance the growth, migration and/or proliferation of cells including tympanic membrane keratinocytes and mucosal cells, over, or into, the device in vivo as it is used as a graft to facilitate closure of a perforation in a tympanic membrane or defective portions of the ear canal for a subject in need of such therapy (see for example FIG. 4). In addition, it is expected that these bioactive molecules would provide biological signals to allow for post healing remodelling of the wound site with the intention to restore functionality to that of a substantially premorbid state, thereby enhancing healing and hearing outcomes in the long term for said subject. The device of the invention may not include bioactive molecules; however, the closure time for repairing a tympanic membrane or an ear canal in a subject in need of such therapy may be reduced when compared to use of a device comprising bioactive molecules.

Biodegradability

It is preferred that a device of the invention would possess an in vivo biological life of between 1 to 12 months, although one or more membranes with a shorter or longer in vivo biological life may also be used in the device. An in vivo biological life of between 1 to 12 months is preferred because the device must remain in place until such a time that complete or substantially complete wound closure has occurred. Typically in tissue engineering it is advantageous to have the device in vivo for a minimal amount of time to prevent possible long term complication such as cyst formation. For example, small perforations may heal in a relatively short period of time (approximately 2 weeks for closure, plus 4-6 weeks for complete remodelling), while larger perforation may take significantly longer requiring up to 12 months for complete cellular remodelling of the neo-tympanum. The biomechanical properties of the device have been selected to substantially prevent atrophy and retraction including cholesteatoma in a subject treated using the device.

An advantage of using the device of the invention is that it reduces donor harvesting operations for autografts and as it can be mass-produced, therefore, reduces operation time and post-surgical recovery for a subject receiving treatment for a perforated tympanic membrane or reconstruction of an ear canal.

Kits

The device of the invention may be provided in the form of a kit for the facilitation of the repair of a tympanic membrane or reconstruction of an ear canal. In this respect, the device in the kit may be provided in a wrapping or a container and in a sterile form. The kit may comprise one or more devices of the same or different sizes and any other medical device, disposable or drug that would facilitate repair of a tympanic membrane or ear canal. Preferably, a device in the kit would be provided in a sterile container or wrapping separate from the remainder of the kit contents. The kit may also comprise a support for the device of a natural or synthetic material, for example, amongst others, a plastic film or sheet. Said disposables may include one or more of bandages, sterilization means for sterilizing the tympanic membrane and the surrounding skin, gloves, sterile sheets, swabs, antibiotic cream or ointment. In one embodiment, said kit comprises at least one device and one or more bioactive molecules. The kit may also comprise bioactive molecules for applying to the device prior to implantation or grafting to the subject. The bioactive molecules may be in the form of one or more solutions. In addition or alternatively, the bioactive molecules may be applied to the ear drum of the subject being treated with the device after the device has been implanted or grafted. This may be immediately and/or in a sequence of treatments over a period of hours or days after implantation.

Method of Use

The invention further provides a method for repairing a tympanic membrane perforation in a subject in need of such treatment, said method comprising using the device of the invention as described herein.

The invention provides that the use of the device to repair a tympanic membrane perforation may be the sole treatment of the tympanic membrane, or may be in addition to other therapies or treatments used simultaneously or concomitantly in the course of treating or repairing a tympanic membrane. For example, the invention provides for the repair of a tympanic membrane comprising contacting the tympanic membrane with the device, and treating the tympanic membrane using an additional therapy not comprising contacting the tympanic membrane with the device, wherein the contacting and the additional therapy individually or together cause a measurable improvement in, maintenance of, or lessening of the worsening of, at least one aspect of tympanic membrane damage.

The device of the invention may be used in tympanic membrane or ear drum perforations involving all parts of the drum and may be used as an onlay, underlay or even inlay technique as is known in the art with existing techniques using an autograft from the subject.

The invention also provides a method for use in the reconstruction of the ear canal including a defective pars flaccida in a subject in need of such treatment, said method comprising using the device of the invention as described herein. The pars flaccida, also commonly referred to as the attic, is technically part of the ear drum, and this is the region typically involved in cholesteatoma which also erodes the surrounding bone of the ear canal called the scutum. Thus, reconstruction of the eardrum in cholesteatoma using the device of the invention, often requires reconstruction of the attic and the surrounding scutum bone which are close and interconnected.

Thus, this treatment may be in conjunction with the repair of a tympanic membrane perforation. Alternatively, the treatment may be to reconstruct the ear canal of a subject that does not have or does not require repair of a tympanic membrane perforation.

The invention also provides for the use of a device as described herein for supporting proliferation, migration and/or adhesion of at least cells of the ear drum when grafted or implanted into the ear drum, and specifically the tympanic membrane, and/or pars flaccida or scutum bone of a subject.

In ear surgery, reconstruction of the bony ear canal following mastoidectomy is commonly required. The device may be used in the reconstruction of the scutum of a subject in need of such treatment. A benefit of using the device of the invention in this reconstruction process is that it can integrate and assist the blood supply into the area through its porous structure, and biomolecules in the device can promote growth of the subjects own cells and tissues into the reconstructed area.

In addition, the device of the invention may be used to repair or in the regeneration of the floor of the ear canal which may be diseased or damaged such as during a range of mastoid operations including mastoidectomy, for example, tympanomastoidectomy for chronic otitis media. In this respect, mastoid obliteration is indicated following canal wall-down tympanomastoidectomy for chronic otitis media to reduce the size of mastoid cavity. Other indications of tympanomastoid or mastoid obliteration include reconstruction of temporal bone resection (secondary to trauma or tumour) and cerebrospinal fluid leaks. Without obliteration, a canal wall-down mastoid cavity can result in persistent otorrhea, frequent cleaning of the cavity, difficulty with the use of a hearing aid, water intolerance due to a susceptibility to infection, and propensity to vertigo. The majority of obliteration techniques consist of either local flaps (e.g. muscle, periosteum, or fascia) or free grafts (e.g. bone chips or pate, cartilage, fat, or ceramic materials such as hydroxyapatite). Whilst hydroxyapatite is the main allograft material, this needs to be covered by viable tissue in the healing phase. Allografts such as plastic mesh, proplast and porous polypropylene had not been successful long term due to infection. Proplast was found to be associated with lasting giant cell reaction. Fistulas, persistent drainage and granulation tissue lead to gradual disuse of plastics. Finally, aloplast is devoid of cancellous bone and its stem cells and has marginal vascularity.

Thus, a device of the invention can be used in mastoid obliteration techniques for reconstruction after tympanomastoidectomy to cover a hydroxyapatite free graft.

Another benefit of the device is that it can provide rigidity and stability which, in the hostile middle ear environment found after surgery, makes it very useful in cases of cholesteatoma, atelectasis and recurrent perforations.

The claims defining the invention are as follows:

1. A device suitable for repair of a tympanic membrane in a subject in need of such treatment, said device:
   (a) having a tensile strength between 12.5 and 40 MPa; and
   (b) comprising one or more membrane layers, wherein at least one membrane layer comprises a plurality of pores with a pore diameter of between approximately 0.001 microns and 1 micron, within and on a surface of the device that facilitate cellular adhesion of cells and proliferation of the cells across the device while preventing infiltration of keratinocytes through the device; and
   (c) wherein the one or more membrane layers have a combined thickness of between approximately 10 μm and approximately 600 μm; and wherein
(i) the device transmits sound waves between 20 Hz and 20 kHz;
(ii) the material forming one or more membrane layers is of a source non-autologous to the subject being treated with the device and is biocompatible; and
(iii) the device supports proliferation, migration and/or adhesion of cells selected from the group comprising at least any one or more of: keratinocytes, fibroblasts, vascular cells, mucosal epithelial cells, and stem cells.

2. A device according to claim 1 having a tensile strength between approximately 15 and approximately 37 MPa.

3. A device according to claim 1 having a tensile strength between approximately 25 and approximately 35 MPa.

4. A device according to claim 1 comprising one or more materials that are non-autologous to the subject in need of such treatment; said material being selected from the group comprising: silk fibroin; hyaluronic acid based hydrogels and films; calcium alginate; alginic acid; pluronic 127; poly(glycerol sebacate); collagen (type I/III); water soluble and insoluble chitosan; gelatin; polyethylene glycol; or decellularised tissue from mammalian membranes, including tympanic membrane, pericardium, periosteum, dermis, and muscle fascia.

5. A device according to claim 4, which incorporates an additive that allows manipulation of the device when in a dry state.

6. A device according to claim 5 wherein the material is silk fibroin.

7. A device according to claim 5 wherein the material is collagen type I/III.

8. A device according to claim 5 comprising bioactive molecules that assist or promote the growth of the cells.

9. The device of claim 8, wherein the bioactive molecules comprises hyaluronic acid.

10. A device according to claim 5 wherein the additive is one or more materials selected from the group consisting of collagen, gelatin, chitosan, alginic acid, hyaluronic acid hydrogels, pluronic 127 and polyethylene glycol.

11. A device according to claim 1, wherein the membrane is folded to match the size of the defective portion of the ear canal.

12. A device according to claim 1 that is at least partially translucent.

13. A device according to claim 1, wherein the surface of one or both faces of the device is scored or grooves are cut to improve the flexibility of the device.

14. A device according to claim 1 wherein the device is formed by at least any one or more of: spinning including electrospinning; weaving including microweaving; or casting.

15. A device according to claim 1, which is suitable for use in repair of tympanic membrane perforation, reconstruction of the ear canal including a defective pars flaccida, the attic and or the surrounding scutum bone, a mastoidectomy including tympanomastoidectomy.

16. A device according to claim 1 wherein the one or more membrane layers include silk fibroin.

17. A device according to claim 16 wherein the one or more materials also include one or more additives selected from the group consisting of: hyaluronic acid based hydrogels and films; calcium alginate; alginic acid; pluronic 127; poly(glycerol sebacate); collagen (type I/III); water soluble and insoluble chitosan; gelatin; polyethylene glycol; or decellularised tissue from mammalian membranes, including tympanic membrane, pericardium, periosteum, dermis, and muscle fascia.

18. The device according to claim 1 wherein, when the device is employed for use in a subject in need of treatment therefrom, the device effectuates repair of the tympanic membrane in the subject.

19. A kit for use in the repair of a tympanic membrane or reconstruction of an ear canal, said kit comprising the device according to claim 1.

20. The kit according to claim 19, further comprising a solution of one or more bioactive molecules that assist or promote the growth of the cells, wherein said solution is applied to the device prior to treatment of a subject with the device.

* * * * *